(12) United States Patent
Gore et al.

(10) Patent No.: US 10,780,048 B2
(45) Date of Patent: Sep. 22, 2020

(54) SUSPENSION COMPOSITIONS OF CYCLOSPORIN A FOR SUBCONJUNCTIVAL AND PERIOCULAR INJECTION

(71) Applicant: Allergan, Inc., Irvine, CA (US)

(72) Inventors: Anuradha V. Gore, Aliso Viejo, CA (US); Hao Hou, Irvine, CA (US); Chetan P. Pujara, Irvine, CA (US); Sesha Neervannan, Irvine, CA (US); Ke Wu, Irvine, CA (US)

(73) Assignee: ALLERGAN, INC., Irvine, CA (US)

(*) Notice: Subject to any disclaimer, the term of this patent is extended or adjusted under 35 U.S.C. 154(b) by 0 days.

(21) Appl. No.: 14/804,011

(22) Filed: Jul. 20, 2015

(65) Prior Publication Data

US 2016/0015632 A1    Jan. 21, 2016

Related U.S. Application Data

(60) Provisional application No. 62/026,200, filed on Jul. 18, 2014.

(51) Int. Cl.
| | |
|---|---|
| *A61K 38/08* | (2019.01) |
| *A61K 9/00* | (2006.01) |
| *A61K 9/10* | (2006.01) |
| *A61K 47/10* | (2017.01) |
| *A61K 38/13* | (2006.01) |
| *A61K 47/36* | (2006.01) |
| *A61K 47/02* | (2006.01) |
| *A61K 47/26* | (2006.01) |
| *A61K 47/38* | (2006.01) |
| *B65D 81/32* | (2006.01) |

(52) U.S. Cl.
CPC .......... *A61K 9/0051* (2013.01); *A61K 9/0048* (2013.01); *A61K 9/10* (2013.01); *A61K 38/13* (2013.01); *A61K 47/02* (2013.01); *A61K 47/10* (2013.01); *A61K 47/26* (2013.01); *A61K 47/36* (2013.01); *A61K 47/38* (2013.01); *B65D 81/32* (2013.01)

(58) Field of Classification Search
None
See application file for complete search history.

(56) References Cited

U.S. PATENT DOCUMENTS

| | | | |
|---|---|---|---|
| 5,252,319 A | 10/1993 | Babcock et al. | |
| 6,677,304 B2 * | 1/2004 | Di Napoli | A61K 9/0048 514/20.5 |
| 8,772,245 B2 * | 7/2014 | Gore | C07K 7/645 514/20.5 |
| 8,785,394 B2 | 7/2014 | Blanda et al. | |
| 8,796,221 B2 | 8/2014 | Wu et al. | |
| 8,796,222 B2 | 8/2014 | Gore et al. | |
| 2001/0041671 A1 | 11/2001 | Napoli | |
| 2008/0057129 A1 * | 3/2008 | Lerner | A61K 9/0075 424/489 |
| 2008/0146497 A1 | 6/2008 | Graham et al. | |
| 2008/0207494 A1 | 8/2008 | Chang et al. | |
| 2013/0040895 A1 | 2/2013 | Robinson et al. | |
| 2013/0122059 A1 | 5/2013 | Gore et al. | |
| 2013/0123194 A1 | 5/2013 | Blanda et al. | |
| 2014/0031298 A1 | 1/2014 | Hughes et al. | |

FOREIGN PATENT DOCUMENTS

| | | |
|---|---|---|
| WO | 1993-023010 | 11/1993 |
| WO | 1995-031211 | 11/1995 |
| WO | 2003-070219 | 8/2003 |
| WO | 2012-166610 | 12/2012 |

OTHER PUBLICATIONS

Bauer, JF Pharmaceutical Solids: Size Shape, and Surface Area, Journal of Validation Technology, 2009 pp. 37-44.*
Fincher, JH., Particle Size of Drugs and its Relationship to Absorption and Activity, Journal of pharmaceutical Sciences, vol. 57, 1968, pp. 1825-1835.*
Virtanen, S et al, Granule Size Distribution of Tablets, Journal of Pharmaceutical Sciences, vol. 99, No. 4, Apr. 2010, pp. 2061-2069.*
Notification of Transmittal of the International Search Report and the Written Opinion of the International Searching Authority, or the Declaration, International Application No. PCT/US2015/041166, International Filing Date Jul. 20, 2015, dated Sep. 4, 2015.
Loosli et al, The Conformation of Cyclosporin A in the Crystal and in Solution, Helvetica Chimica Acta, 1985, 682-704, 68.
Masuda, K, et al, Double-Masked Trial of Cyclosporin Versus Cohlchicine and Long-Term Open Study of in Cyclosporin Behcet's Disease, The Lancet, May 20, 1989, 1093-1096, vol. 333, Issue 8647.

* cited by examiner

Primary Examiner — Thomas S Heard
(74) Attorney, Agent, or Firm — Lorenz Siddiqi

(57) ABSTRACT

The present disclosure relates to suspension formulations and systems for the treatment of ocular conditions. The suspension formulations can include cyclosporin A and in some embodiments, Form 1 or Form 2 cyclosporin A. A delivery system can be provided that includes two parts, a first part containing particles of cyclosporin and a second part containing other components that can be combined with the first part to make a suspension formulation. The suspension can be injected into the subconjunctival or other periocular space to treat ocular conditions, such as dry eye disease.

5 Claims, 9 Drawing Sheets

SUSPENSION COMPOSITIONS OF CYCLOSPORIN A FOR SUBCONJUNCTIVAL AND PERIOCULAR INJECTION

CROSS-REFERENCE TO RELATED APPLICATIONS

This application claims the benefit of U.S. Provisional Application No. 62/026,200 filed on Jul. 18, 2014, the entire content of which is incorporated herein by reference.

BACKGROUND

Field

This disclosure relates generally to formulations for sustained delivery of active agents, for example, different forms of cyclosporin A.

Description of the Related Art

Cyclosporin, a cyclic peptide containing 11 amino acids with a total molecular weight of 1202 Daltons, has long been known as a potent immunosuppressant and anti-inflammatory agent. In ophthalmology, systemic cyclosporin A has been used to treat conditions such as severe posterior segment inflammation (Masuda et al, 1989), ulcerative keratitis associated with Wegener's granulomatosis, severe Grave's ophthalmopathy, and graft rejection after keratoplasty.

More recently, cyclosporin has been used in conventional treatment of certain ocular surface disorders, for example dry eye disease or keratoconjunctivitis sicca, which can require daily multiple applications of eye drops. For example, RESTASIS® Cyclosporin Ophthalmic Emulsion 0.05% is indicated to increase tear production in patients whose tear production is presumed to be suppressed due to ocular inflammation associated with keratoconjunctivitis sicca.

However, there are shortcomings of topical eye drop formulations. Often patient compliance rate for regular, daily use of eye drops is low. Additionally, eye irritation and infection can result from improper eye dropper use. Hence, there is a need for a long term (e.g. sustained release) treatment method for ocular disorders, such as dry eye or keratoconjunctivitis sicca that can be administered by a healthcare professional.

SUMMARY

Accordingly, an embodiment provides a suspension formulation for subconjunctival injection into the eye of a human. The suspension formulation can include cyclosporin A, a suspending agent, an osmolality agent, one or more buffer, a surfactant, and a vehicle. In some embodiments, the cyclosporin A is one or more of Form 1 cyclosporin A, Form 2 cyclosporin A, or amorphous cyclosporin A. In some embodiments, the cyclosporin A is Form 2 cyclosporin A. According to some embodiments, the Form 2 cyclosporin A is substantially free of other forms of cyclosporin A. In some embodiments, the suspending agent can be selected from hyaluronic acid, carboxymethyl cellulose, hydroxyethyl cellulose, hydroxypropyl methylcellulose, polyvinylpyrrolidone K90, pluronic F127, and carbomer. In some embodiments, the osmolality agent can be selected from sodium chloride, potassium chloride, and mannitol. According to some embodiments, the one or more buffer can be selected from phosphate buffer, phosphate citrate buffer, sodium hydroxide, trolamine, lactate buffer, borate buffer, and borate citrate. In some embodiments, the surfactant can be selected from polysorbate 80, solutol HS 15, pluronic F68, pluronic F127, Cremophor RH40, Cremophor EL, and sodium glycocholate. In an embodiment, the cyclosporin A is present in the suspension formulation in an amount in the range of about 5% w/w to about 20% w/w. In another embodiment, the cyclosporin A is present in the suspension formulation in an amount of about 20% w/w. In yet another embodiment, the cyclosporin A is present in the suspension formulation in an amount of about 10% w/w. In an embodiment, the Form 1 cyclosporin A has a $D_{90}$ particle size in the range of about 70 µm to about 100 µm. In some embodiments, the suspension formulation includes a pre-filled syringe, wherein the suspension formulation is contained inside the pre-filled syringe. According to an embodiment, the suspension formulation can be frozen at a temperature in the range of about −70° C. to about −2° C.

Accordingly, another embodiment provides a two-part system for making a suspension for subconjunctival injection. The two-part system can include a first part that contains cyclosporin A and a second part that includes water, one or more buffer, a suspending agent, an osmolality agent, and a surfactant. In some embodiments, the cyclosporin A is selected from Form 1 cyclosporin A or Form 2 cyclosporin A. The first part and the second part can be in separate containers. In some embodiments, the suspending agent can be selected from hyaluronic acid, carboxymethyl cellulose, hydroxyethyl cellulose, hydroxypropyl methylcellulose, polyvinylpyrrolidone K90, pluronic F127, and carbomer. In some embodiments, the osmolality agent can be selected from sodium chloride, potassium chloride, and mannitol. According to some embodiments, the one or more buffer can be selected from phosphate buffer, phosphate citrate buffer, sodium hydroxide, trolamine, lactate buffer, borate buffer, and borate citrate. In some embodiments, the surfactant can be selected from polysorbate 80, solutol HS 15, pluronic F68, pluronic F127, Cremophor RH40, Cremophor EL, and sodium glycocholate. In an embodiment, the cyclosporin A is present in the suspension formulation in an amount in the range of about 5% w/w to about 20% w/w. In another embodiment, the cyclosporin A is present in the two-part system in an amount of about 5% w/w. In yet another embodiment, the cyclosporin A is present in the two-part system in an amount of about 10% w/w. In yet another embodiment, the cyclosporin A is present in the two-part system in an amount of about 20% w/w. In an embodiment, the cyclosporin A is Form 1 cyclosporin A, and the Form 1 cyclosporin has a $D_{90}$ particle size in the range of about 70 µm to about 100 µm.

Accordingly, yet another embodiment provides a two-part system for making a suspension for subconjunctival injection. The two-part system can include a first part that includes Form 1 cyclosporin A, a first surfactant, a bulking agent, and a first suspending agent and a second part that includes water and one or more buffer. The first and second parts can be in separate containers. In some embodiments, the first suspending agent can be selected from hyaluronic acid, carboxymethyl cellulose, hydroxyethyl cellulose, and hydroxypropyl methylcellulose and the second suspending agent can be selected from hyaluronic acid, carboxymethyl cellulose, hydroxyethyl cellulose, and hydroxypropyl methylcellulose. According to another embodiment, the one or more buffer can be selected from phosphate buffer, phosphate citrate buffer, sodium hydroxide, trolamine, lactate buffer, borate buffer, and borate citrate. In some embodiments, the first surfactant can be selected from polysorbate 80, solutol HS 15, pluronic F68, pluronic F127, Cremophor RH40, Cremophor EL, and sodium glycocholate. The bulking agent can be mannitol. In an embodiment, the Form 1 cyclosporin A has a $D_{90}$ particle size in the range of about 70 µm to about 100 µm.

DETAILED DESCRIPTION

Figure 1:
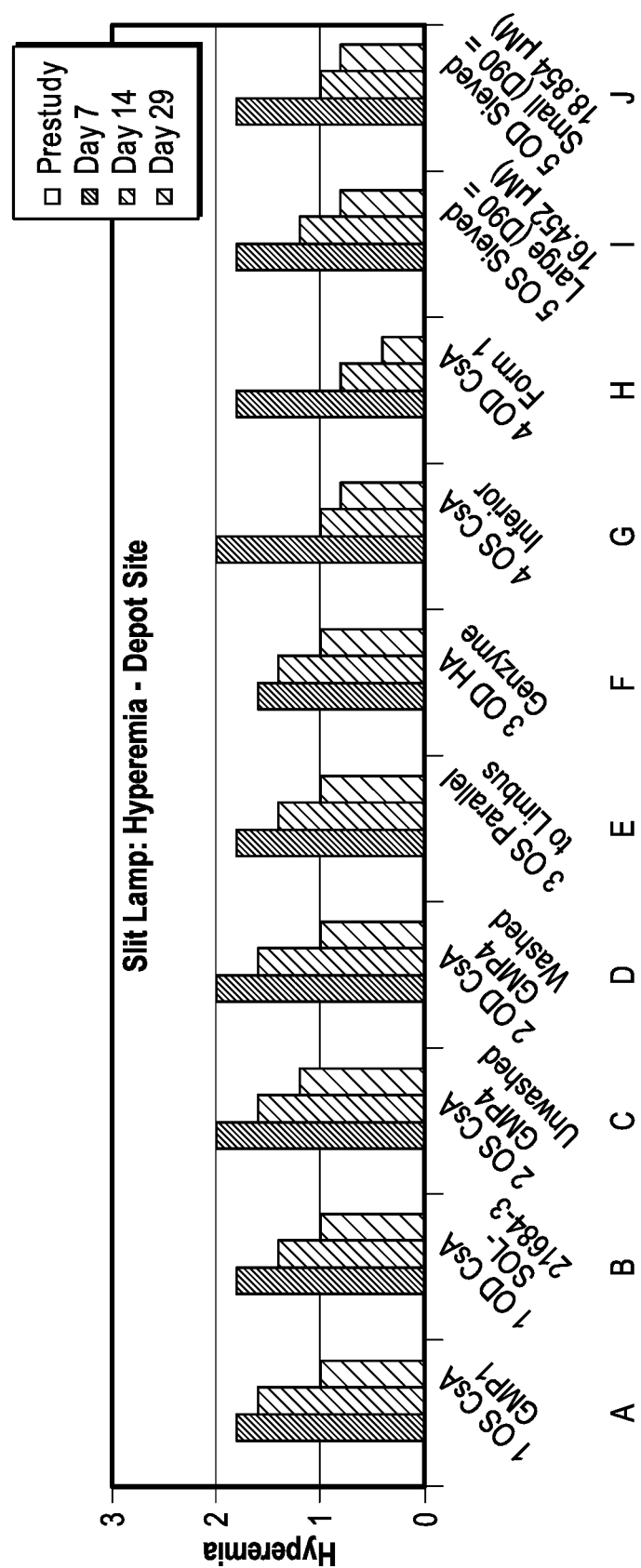
FIG. 1 illustrates a comparison of hyperemia scores at the depot site of various embodiment suspension formulations used in the study according to Example 1.

In general terms, an embodiment relates to cyclosporin A sustained delivery for therapeutic applications. In some embodiments, the cyclosporin A is formulated into a suspension for intraocular injection. According to some embodiments, the suspension can be injected into the subconjunctival, sub-tenon, intracameral, intravitreal spaces or the vitreous, where the suspension can effectively treat ocular conditions affecting the anterior or posterior segments of the human eye, such as ocular surface disorders.

Embodiments herein disclose new drug delivery systems, and methods of making and using such systems, for extended or sustained drug release into an eye, for example, to achieve one or more desired therapeutic effects. The drug delivery systems can be in the form of suspension formulations that can be injected into an eye. The systems and methods disclosed in some embodiments herein can provide for extended release time of one or more therapeutic agent or agents. Thus, for example, a patient who has received such a suspension injected into their eye can receive a therapeutic amount of an agent for a long or extended time period without requiring additional administrations of the agent.

As used herein, the terms "cyclosporin" or "cycosporin A" or "CsA" shall refer to cyclosporin A, cyclosporine, cyclosporine A, ciclosporin, ciclospoin A, CsA, and the like. Unless specified, the terms "cyclosporin" or "cyclosporin A" or "CsA" used generally refers to cyciosporin A and each of its polymorphs described herein (e.g. Form 1 cyclosporin A (also referred to as "cyclosporin A Form 1" or "CsA F1"), Form 2 cyclosporin A (also referred to as "cyclosporin A Form 2" or "CsA F2"), amorphous cyclosporin A) individually and/or mixtures thereof. In some embodiments, the different crystalline forms of cyclosporin A may be substantially free of other forms of cyclosporin A.

As used herein, an "ocular condition" is a disease ailment or condition which affects or involves the eye or one of the parts or regions of the eye. The eye can include the eyeball and the tissues and fluids that constitute the eyeball, the periocular muscles (such as the oblique and rectus muscles) and the portion of the optic nerve which is within or adjacent the eyeball. An ocular condition can include an ocular surface disorder, such as dry eye, keratoconjunctivitis sicca, ocular graft versus host disease, meibomian gland disease, blepharitis, evaporative dry eye, and the like.

As used herein, the term "suspension" refers to formulations that include a dispersion of particles in a liquid carrier. In some embodiments, these particles can settle and may need to be redispersed through agitation.

The terms "treat", "treating", or "treatment" as used herein, refer to reduction or resolution or prevention of an ocular condition, ocular injury or damage, or to promote healing of injured or damaged ocular tissue.

The term "therapeutically effective amount" as used herein, refers to the level or amount of therapeutic agent needed to treat an ocular condition, or reduce or prevent ocular injury or damage.

Those skilled in the art will appreciate the meaning of various terms of degree used herein. For example, as used herein in the context of referring to an amount (e.g., "about 6%"), the term "about" represents an amount close to and including the stated amount that still performs a desired function or achieves a desired result, e.g. "about 6%" can include 6% and amounts close to 6% that still perform a desired function or achieve a desired result. For example, the term "about" can refer to an amount that is within less than 10% of, within less than 5% of, within less than 0.1% of, or within less than 0.01% of the stated amount.

Cyclosporin A

Suspensions disclosed herein can contain a cyclosporin A component. Cyciosporin A (CsA) is a cyclic peptide having the following chemical structure:

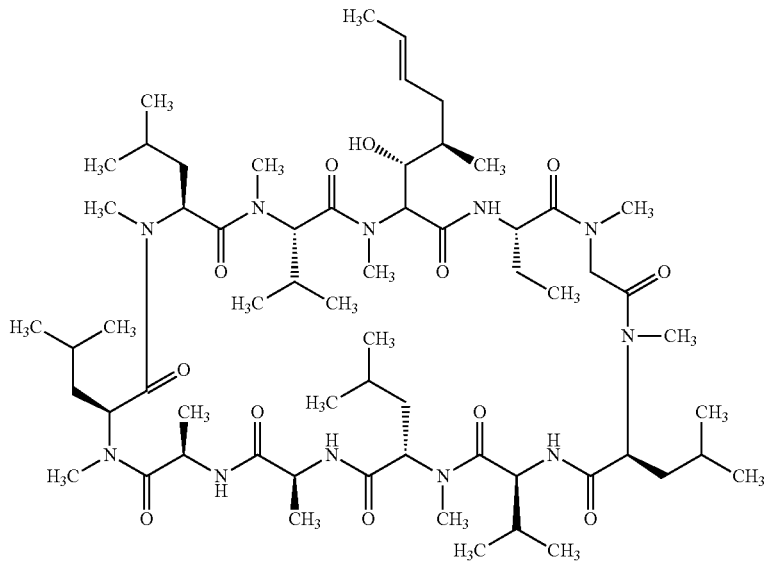 [SMILES: C/C=C/C[C@@H](C)[C@@H](O)C1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Its chemical name is Cyclo[[(E)—(2S,3R,4R)—3—hydroxy—4—methyl—2—(methylamnio)—6—octenoyl]—L—2—aminobutyryl—N—methylglycyl—N—methylL—leucyl—L—valyl—N—methyl—L—leucyl—L—alanyl—D—alanyl—N—methyl—L—L—leucyl—N—methyl—L—L—leucyl—N—methyl—L—valyl]. It is also known by the names cyclosporine, cyclosporine A, ciclosporin, and ciclosporin A. It is the active ingredient in RESTASIS® (Allergan, Inc., Irvine, Calit), an emulsion comprising 0.05% cyclosporin.

Cyclosporin A is known to exist in an amorphous form, liquid crystal form, tetragonal dihydrate crystalline form (Form 1), a crystalline form (Form 2), and an orthorhombic monohydrate form (Form 3).

Form 1

CsA Form 1 exists in a tetragonal crystalline form. CsA Form 1 has been described in several publications, including "The Conformation of Cyclosporin A in the Crystal and in Solution" Loosh, et al, Helvetica Chimica Acta. Vol. 68 (1985), which is incorporated by reference. The summary of the crystal data and diffractometry of Form 1 is shown in the table below.

CsA Form 1 is a dihydrate of Cyclosporin A. This form can only forms in acetone-containing solvent systems. Form 1 may undergo dehydration and lose crystallinity upon exposure to heating, vacuum drying, or mechanical stress. In addition, Form 1 tends to convert to amorphous material in aqueous environment. The kinetics of the conversion is temperature dependent with higher temperature favoring accelerated transformation.

TABLE 5

Crytal and Diffraction Data

| Molecular formula | $C_{62}H_{111}N_{11}O_{12}$ | Molecules per cell | Z = 4 |
|---|---|---|---|
| Molecular weight | 1202.5 | Diffractometer | CAD4 (Enraf- Nonius) |
| Crystallisation | from acetone | Radiation | $CuK_\alpha$ (Graphite Monochromator) |
| Crystal form | colourless, prismatic | Intensity scans | $\omega/2\theta = 1.0; \Delta\omega = 1.0° + 0.3 \tan\theta$ |
| Crystal size | ca. 0.2 × 0.2 × 0.3 mm | | $\sigma(I)/I = 0.02$ ($t_{max} = 120$ s) |
| Space group | $P4_1$ (No 76) | Sphere of reflexion | $\sin\theta/\lambda < 0.51$ (36508 reflexions) |
| Cell dimensions | a = b = 13.837 (2), | Intensities measured | 5057 (unique) |
| | c = 41.242 (3) Å; V = 7896 Å$^3$ | intensities significant | 4272 (I > 2.5σ(I)); |
| Crystal density (calc.) | $d_c = 1.042$ g · cm$^{-3}$ | | $\sigma(I) = \{\Sigma i_n + 0.02 \cdot I\}^{1/2}$ |

Form 2

The XRPD pattern of CsA Form 2 differs significantly from the tetragonal dihydrate form and orthorhombic form monohydrate form. The major crystalline peaks for CsA Form 2 appear at (2θ) when scanned by an X-ray diffractometer with X-ray source as Cu Kα radiation, λ=1.54 Å, at 30 kV/15 mA: 7.5, 8.8, 10.2, 11.3, 12.7, 13.8, 14.5, 15.6 and 17.5 (d-spacing in crystal lattice at about 11.8, 10.0, 8.7, 7.8, 7.0, 6.4, 6.1, 5.6 and 5.1 Å.) These major peaks are defined as those being unique to Form 2 relative to the orthorhombic monohydrate or tetragonal dihydrate forms; as well as, peaks having intensity greater than 5 times the background.

In one embodiment, Form 2 CsA is a nonstoichiometric hydrate of Cyclosporin A. In another embodiment, the crystalline Form 2 is represented by the formula:

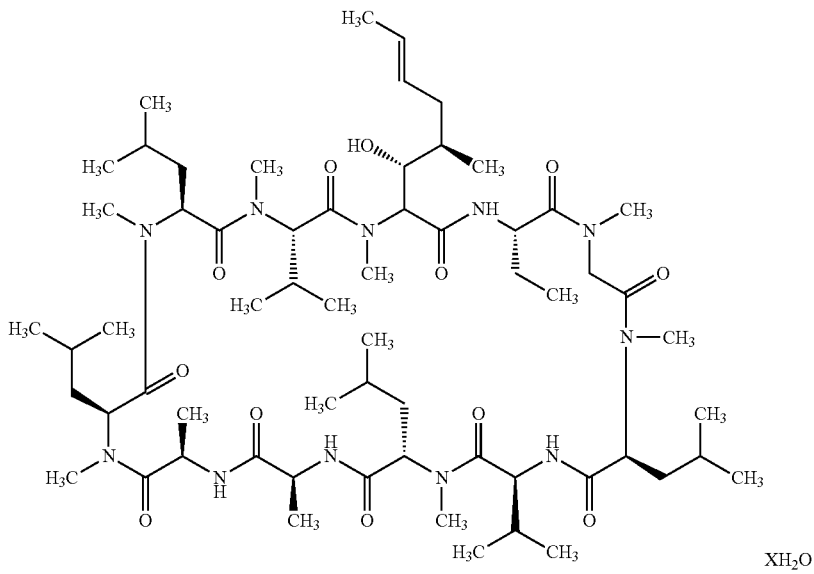

wherein X is the number of molecules of water and varies from 0 to 3. In one embodiment, X in the above formula is 2.

Form 2 appears to be a kinetically stable form of CsA in aqueous suspensions. Suspensions containing Form 2 show no conversion to other known polymorphic or pseudomorphic forms upon storage.

The single crystal structure of the hydrate form of CsA Form 2 has been determined and the crystal structure parameters are listed in Table 2. These results indicate that Form 2 is unique compared to other known crystalline forms of cyclosporin A.

TABLE 1

Crystal data and data collection parameters of crystal structure solution of CsA Form 2.

| | |
|---|---|
| formula | $C_{62}H_{118}N_{11}O_{14}$ |
| formula weight | 1238.67 |
| space group | $P\ 2_1\ 2_1\ 2_1$ (No. 19) |
| a (Å) | 12.6390(5) |
| b (Å) | 19.7582(8) |
| c (Å) | 29.568(2) |
| volume (Å$^3$) | 7383.8(7) |
| Z | 4 |
| $d_{calc}$ (g cm$^{-3}$) | 1.114 |
| crystal dimensions (mm) | 0.27 × 0.18 × 0.12 |
| temperature (K) | 150 |
| radiation (wavelength in Å) | Cu K$_3$(1.54184) |
| monochromator | confocal optics |
| linear abs coef (mm$^{-1}$) | 0.640 |
| absorption correction applied | empirical$^a$ |
| transmission factors (min, max) | 0.80, 0.93 |
| diffractometer | Rigaku RAPID-II |
| h, k, l range | −13 to 13 −21 to 21 −32 to 21 |
| 2θ range (deg) | 5.38-115.00 |
| mosaicity (deg) | 1.31 |
| programs used | SHELXTL |
| $F_{coc}$ | 2704.0 |
| weighting | $1/[\sigma^2(Fo^2) + (0.0845P)^2 + 0.0000P]$ where P = (Fo$^2$ + 2Fc$^2$)/3 |
| data collected | 37360 |
| unique data | 9964 |
| $R_{ml}$ | 0.077 |
| data used in refinement | 9964 |
| cutoff used in R-factor calculations | Fo$^2$ > 2.0 s(Fo$^2$) |
| data wiith I > 2.0 s(I) | 6597 |
| number of variables | 834 |
| largest shift/esd in final cycle | 0.00 |
| R(F$_0$) | 0.061 |
| R$_g$(Fo$^2$) | 0.145 |
| goodness of fit | 1.037 |
| absolute structure determination | Flack parameter$^a$(0.0(3)) |

The asymmetric unit of this CsA Form 2 contains one cyclosporin A molecule and two water molecules. It is possible that any small molecule that can hydrogen bond to water could play the role of space filler, which would give a range of potential structures running from the orthorhombic dihydrate to distorted monoclinic dihydrate. The XRPD pattern calculated from the single-crystal structure is shown in FIG. 9 and it matches the experimental pattern shown in FIG. 2. These matching patterns further corroborate that Form 2 is a unique and pure crystalline form of cyclosporin A.

Figure 3:
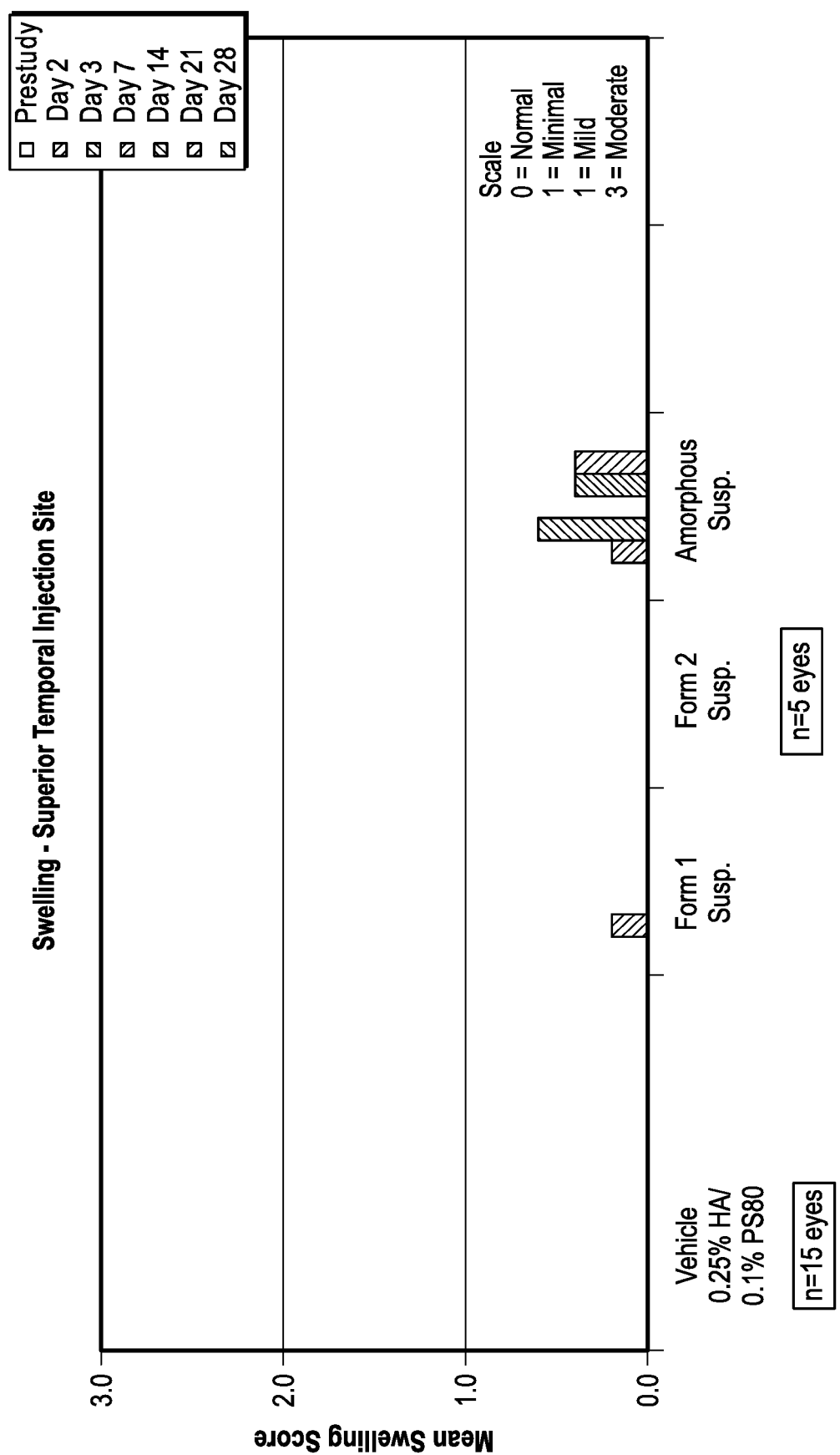
FIG. 3 illustrates a comparison of conjunctival swelling scores at the superior temporal injection site of various embodiment suspension formulations used in the Example 2 study.
Figure 4:
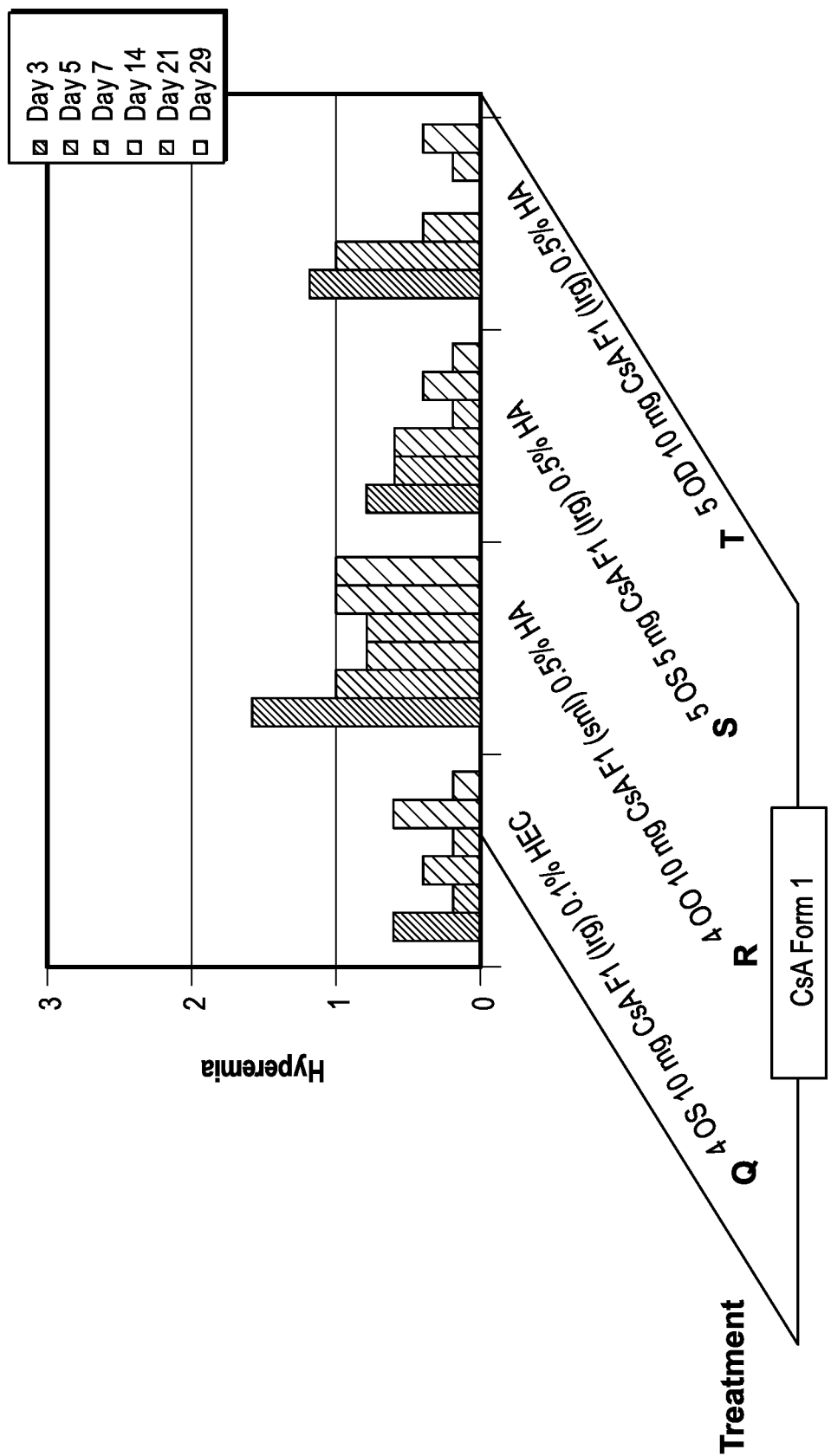
FIG. 4 shows a comparison of conjunctival hyperemia scores for the entire eye of various embodiment suspension formulations used in the Example 3 study.

Without wishing to be bound by theory, thermogravimetric analysis combined with KF titration and vapor sorption desorption analysis (VSA) suggest that CsA Form 2 is a nonstoichiometric hydrate of CsA. The vapor sorption analysis of Cyclosporin A Form 2 indicates that water content in the new crystal form reversibly varies with relative humidity as shown in FIG. 3. Similar to the tetragonal form, the new CsA form undergoes a phase transition to a liquid crystal or amorphous form at 124.4° C. prior to melting as indicated by the modulated differential calorimetric (MDSC) analysis (FIG. 4).

Further details regarding CsA Form 2 may be found in U.S. Pat. Nos. 8,772,245, 8,796,221, 8,785,394, and 8,796,222, the entire contents of which are incorporated by reference herein.

According to some embodiments, suspension formulations described herein can contain cyclosporin A in an amount in the range of 0.1% by weight to 20% by weight, based on the total weight of the suspension formulation. In an embodiment, suspension formulations described herein can contain cyclosporin A component in an amount in the range of 5% by weight to 30% by weight, based on the total weight of the suspension formulation. In some embodiments suspension formulations can contain cyclosporin A in an amount in the range of 1% by weight to 6% by weight, based on the total weight of the suspension formulation. In other embodiments, suspension formulations can contain cyclosporin A in an amount in the range of 15% by weight to 25% by weight, based on the total weight of the suspension formulation. In some embodiments, the suspension formulation may contain cyclosporin A in an amount of about 5% by weight, about 10% by weight, about 15% by weight, about 20% by weight, about 25% by weight, or about 30% by weight, based on the total weight of the suspension formulation.

According to some embodiments, the cyclosporin A is cyclosporin A Form 2. In some embodiments, the suspension formulation includes cyclosporin A Form 2, and the formulation is substantially free of other forms of cyclosporin A. According to some embodiments, the cyclosporin A is cyclosporin A Form 1. In some embodiments, the suspension formulation includes cyclosporin A Form 1, and the suspension formulation is substantially free of other forms of cyclosporin A.

In some embodiments, the particle size distribution of the cyciosporin A used in the suspension formulation can fall within a desired range. In some embodiments, the particle size distribution of the cyclosporin A is in the range of a $D_{50}$ of about 10 μm to a $D_{50}$ about 200 μm. In some embodiments the particle size distribution is in the range of a $D_{90}$ of about 10 μm to a $D_{90}$ of less than about 100 μm. In some embodiments the particle size distribution of the cyclosporin A is in the range of a $D_{90}$ of about 50 μm to a $D_{90}$ of less than about 150 μm. In some embodiments the particle size distribution of the cyclosporin is in the range of a $D_{50}$ of about 10 μm to a $D_{50}$ of less than about 50 μm. In some embodiments, where cyclosporin A Form 1 is used in the suspension formulation, the particle size distribution of cyclosporin A Form 1 is in the range of a $D_{10}$ of 10 μm to a $D_{90}$ of 100 μm. In some embodiments, where cyclosporin A Form 1 is used in the suspension formulation, the particle size distribution of cyclosporin A Form 1 is in the range of a $D_{90}$ of about 50 μm to a $D_{90}$ of less than about 150 μm. In some embodiments, where cyclosporin A Form 2 is used in the suspension formulation, the particle size distribution of cyclosporin A Form 2 is in the range of a $D_{90}$ of about 50 μm to a $D_{90}$ of less than about 75 μm. In some embodiments, the particle size distribution of cyclosporin A Form 2 is in the range of a $D_{50}$ of about 16 μm to a $D_{50}$ of less than about 40 μm.

Suspending Agents/Viscosity Enhancer

In some embodiments, a suspension formulation can further include a suspending agent or a viscosity enhancer. A suspending agent or a viscosity enhancer can include one or more of hydroxypropyl methylcellulose, sodium hyaluronate (hyaluronic acid or "HA"), carboxymethyl cellulose, hydroxyethyl cellulose, polyvinylpyrrolidone K90, pluronic F127 (Poloxamer 407), carbomer, and the like. In some embodiments, only one suspending agent or viscosity enhancer is included in the suspension formulation. In some embodiments, the suspension agent or viscosity enhancer is hyaluronic acid.

According to some embodiments, suspension formulations described herein can contain a suspending agent in an amount in the range of 2% by weight to 20% by weight, based on the total weight of the suspension formulation. In some embodiments suspension formulations can contain a suspending agent in an amount in the range of 1% by weight to 6% by weight, based on the total weight of the suspension formulation. In other embodiments, suspension formulations can contain a suspending agent in an amount in the range of 15% by weight to 25% by weight, based on the total weight of the suspension formulation. In other embodiments, the suspending agent can be present in the formulation in an amount in the range of about 0.1% by weight to about 1.0% by weight, based on the total weight of the suspension formulation. In other embodiments, the suspending agent can be present in the formulation in an amount in the range of about 0.2% by weight to about 0.5% by weight, based on the total weight of the suspension formulation.

Solubilizer/Surfactant/Dispersing Agent

In some embodiments, a suspension formulation can further include a solubilizer/surfactant/dispersing agent. A solubilizer/surfactant/dispersing agent can include one or more of polysorbate 80, solutol HS 15, Pluronic F68, Pluronic F127, Cremophor RH40, Cremophor EL, sodium glycocholate, and the like. In some embodiments, no solubilizer/surfactant/dispersing agent is present.

According to some embodiments, suspension formulations described herein can contain a solubilizer/surfactant/dispersing agent in an amount in the range of 1% by weight to 10% by weight, based on the total weight of the suspension formulation. In some embodiments suspension formulations can contain a solubilizer/surfactant/dispersing agent in an amount in the range of 1% by weight to 6% by weight, based on the total weight of the suspension formulation. In other embodiments, suspension formulations can contain a solubilizer/surfactant/dispersing agent in an amount in the range of 2% by weight to 5% by weight, based on the total weight of the suspension formulation. In other embodiments, suspension formulations can contain a solubilizer/surfactant/dispersing agent in an amount in the range of 0.1% by weight to 1.0% by weight, based on the total weight of the suspension formulation. In other embodiments, suspension formulations can contain a solubilizer/surfactant/dispersing agent in an amount in the range of 0.1% by weight to 0.60% by weight, based on the total weight of the suspension formulation.

Osmolality Agents

In some embodiments, a suspension formulation can further include an osmolality agent. The osmolality agent can include one or more of potassium chloride, mannitol, sodium chloride, and the like. In some embodiments, no osmolality agent is present.

According to some embodiments, suspension formulations described herein can contain an osmolality agent in an amount in the range of 1% by weight to 5% by weight, based on the total weight of the suspension formulation. In some embodiments suspension formulations can contain an osmolality agent in an amount in the range of 1% by weight to 2% by weight, based on the total weight of the suspension formulation. In other embodiments, suspension formulations can contain an osmolality agent in an amount in the range of 2% by weight to 4% by weight, based on the total weight of the suspension formulation. In other embodiments, suspension formulations can contain an osmolality agent in an amount in the range of 0.5% by weight to 1.0% by weight, based on the total weight of the suspension formulation.

Buffers

In some embodiments, a suspension formulation can further include a suitable buffer. A buffer may include phosphate buffer, phosphate citrate buffer, sodium hydroxide/trolamine, a lactate buffer, a borate buffer, borate citrate, and the like. For example, the buffer may include one or more of sodium phosphate dibasic heptahydrate, sodium phosphate monobasic monohydrate, sodium hydroxide, or hydrochloric acid. A buffer can be used to control the pH of the suspension formulations. In some embodiments, the pH of the suspension formulation is in the range of about 6.0 to about 8.0. In some embodiments, the pH of the suspension formulation is about 7.0.

Preservatives

In some embodiments, a suspension formulation can further include a suitable preservative. The preservative may include BAK, purite, and the like. In some embodiments, the suspension formulation contains no preservative or essentially no preservative.

According to some embodiments, suspension formulations described herein can contain a preservative in an amount in the range of 10 ppm-200 ppm by weight, based on the total weight of the suspension formulation. In some embodiments suspension formulations can contain a preservative in an amount in the range of 10 ppm-300 ppm by weight, based on the total weight of the suspension formulation.

Vehicle

In some embodiments, the suspension formulation includes a suitable vehicle, such as water.

Diluent/Bulking Agent/Cake Formers

In some embodiments, the suspension formulation can include one or more diluent/bulking agent/cake former. A diluent/bulking agent/cake former can prevent agglomeration of particles (such as particles of cyclosporin A) in formulations where the cyclosporin may be kept in a powder form and later combined with liquid components to form a cyclosporin suspension. Examples of diluent/bulking agent/cake formers can include mannitol, trehalose, or lactose. In some embodiments, a diluent/bulking agent/cake former can be present in a suspension formulation in the range of about 2% by weight to about 10% by weight. In some embodiments, a diluent/bulking agent/cake former can be present in a suspension formulation in the range of about 3% by weight to about 6% by weight. In some embodiments, no diluent/bulking agent/cake formers are present.

Delivery Systems for Suspension Formulations

In some embodiments, the suspension formulations described herein can be provided to a patient in a suitable delivery system. The delivery system can be, but is not limited to, a pre-filled syringe, a frozen formulation, or a two-part formulation.

According to example embodiments, in a pre-filled syringe formulation, the suspension formulations described herein may be preloaded into a syringe of appropriate size, such as a 22 gauge needle, a 23 gauge needle, a 25 gauge needle, a 27 gauge needle, or a 29 gauge needle. In some embodiments, the pre-filled syringe may have to be shaken or otherwise agitated to redisperse the cyclosporin in the suspension that may have settled over time.

In some embodiments, in a frozen formulation, the suspension formulation is prepared according to methods described herein, then exposed to low temperatures until the suspension is frozen. The particles of cyclosporin A in the frozen suspension can remain in a suspended state until it is needed for injection into a patient's eye. At such a time, the frozen suspension can be thawed out to room temperature. According to some embodiments, a cyclosporin A suspension can be frozen to a temperature in the range of about −70° C. to about −2° C.

In some embodiments, the suspension formulations disclosed herein can be available as a two-part formulation. The two parts of the two-part formulation may be in separate containers, so that the two parts are not combined until necessary for administration. In some embodiments, the first part of a two-part formulation can comprise a powder component and the second part of the two-part formulation can include a liquid component. In some embodiments, the powder component can include cyclosporin A. In some embodiments, the powder component of a two-part formulation can include one or more of a suspending agent/viscosity enhancer, a solubilizer/surfactant/dispersing agent, an osmolality agent, buffer, preservatives, and a diluent/bulking agent/cake former. The powder component may be manufactured by lyophilization, spray-drying, blending, milling, granulation or other pharmaceutical processing. The liquid component can include one or more of a suspending agent/viscosity enhancer, a solubilizer/surfactant/dispersing agent, an osmolality agent, a buffer, preservatives, and a vehicle. For example, a first part of a two-part formulation may comprise, consist of, or consist essentially of cyclosporin A Form 1 or cyclosporin A Form 2, sodium hyaluronate, poloxamer 407, and mannitol in a lyophilized powder formulation. In the same embodiment, the second part of the two-part formulation may include a liquid vehicle for reconstitution comprising, consisting of, or consisting essentially of sodium phosphate dibasic heptahydrate, sodium phosphate monobasic monohydrate, and water. In another embodiment, the first part of the two-part formulation comprises, consists of, or consists essentially of cyclosporin A Form 1 or cyclosporin A Form 2. In the same embodiment, the second part of the two-part formulation may include a liquid vehicle for reconstitution comprising, consisting of, or consisting essentially of sodium hyaluronate, poloxamer 407, sodium phosphate dibasic heptahydrate, sodium phosphate monobasic monohydrate, sodium chloride, and water.

When a two-part formulation is used, the reconstitution of the suspension formulation can be performed by combining the first part of the formulation with the second part of the formulation, then shaking the formulation for an amount of time in the range of about one minute to about ten minutes. In some embodiments the two parts of the two-part suspension formulation can be shaken for an amount of time of about five minutes. In some embodiments, the two-part suspension may be shaken by hand after the first part of the two-part formulation is combined with the second part of the two-part formulation.

Example ranges of components for various example embodiment delivery systems are described in Tables 2-4 below.

TABLE 2

Examples of formulation compositions for prefilled syringe or frozen formulations

| Ingredient type | Ingredient | Examples of conc. range % (w/w) |
|---|---|---|
| Active Ingredients | Cyclosporin | 0.1-30% |
| | Following ingredients may or may not be included in the formulation | |
| Suspending agents/viscosity enhancer (may or may not be required) | Hydroxypropyl Methyl Cellulose | 0-7% |
| | Sodium Hyaluronate | 0-5% |
| | Carboxymethyl Cellulose | 0-8% |
| | Hydroxyethyl Cellulose | 0-6% |
| | Polyvinylpyrrolidone K90 | 0-25% |
| | Pluronic F127 | 0-15% |
| | Carbomer | 0-4% |
| Solubilizer/surfactant/dispersing agents (may or may not be required) | Polysorbate 80 | 0-4% |
| | Solutol HS 15 | 0-5% |
| | Pluronic F68 | 0-5% |
| | Cremophor RH40 | 0-5% |
| | Cremophor EL | 0-5% |
| | Sodium glycocholate | 0-2% |
| | Pluronic F127 | 0-2% |
| Osmolality agents (any one or two or more in combinations) | Potassium chloride | 0-2% |
| | Mannitol | 0-5% |
| | Sodium chloride | 0-1% |
| Buffers (Any one or more of the buffers listed) | Phosphate buffer | *q.s. for 1-100 mM |
| | Phosphate citrate buffer | *q.s. for 1-100 mM |
| | NaOH/Trolamine | *q.s. for 1-100 mM |
| | Lactate buffer | *q.s. for 1-100 mM |
| | Borate buffer | *q.s. for 1-100 mM |
| | Borate citrate | *q.s. for 1-100 mM |
| Preservatives | None - Non preserved | NA |
| | BAK | 10-200 ppm |
| | Purite | 10-300 ppm |
| Vehicle | Water | QS |
| pH range | n/a | pH 5 to 8 |

TABLE 3

Examples of Part 1 as drug substance with other excipients in powder form for a two-part formulation system. Composition is based on the total weight of the suspension formulation.

| Ingredient type | Ingredient | Examples of typical conc. range % (w/w) |
|---|---|---|
| Active Ingredients | Cyclosporin | 0.1-30% |
| | Following ingredients may or may not be included in the formulation Part 1 | |
| Suspending agents/viscosity enhancer (may or may not be required) | Hydroxypropyl Methyl Cellulose | 0-7% |
| | Sodium Hyaluronate | 0-5% |
| | Carboxymethyl Cellulose | 0-8% |
| | Hydroxyethyl Cellulose | 0-6% |
| | Polyvinylpyrrolidone K90 | 0-25% |
| | Pluronic F127 | 0-15% |
| | Carbomer | 0-4% |
| Solubilizer/surfactant/dispersing agents (may or may not be required) | Polysorbate 80 | 0-4% |
| | Solutol HS 15 | 0-5% |
| | Pluronic F68 | 0-5% |
| | Cremophor RH40 | 0-5% |
| | Cremophor EL | 0-5% |
| | Pluronic F127 | 0-2% |
| | Sodium glycocholate | 0-2% |
| Osmolality agents (any one or two or more in combinations) | Potassium chloride | 0-2% |
| | Mannitol | 0-5% |
| | Sodium chloride | 0-1% |

TABLE 3-continued

Examples of Part 1 as drug substance with other excipients in powder form for a two-part formulation system. Composition is based on the total weight of the suspension formulation.

| Ingredient type | Ingredient | Examples of typical conc. range % (w/w) |
|---|---|---|
| Buffers (Any one or more of the buffers listed) | Phosphate buffer | *q.s. for 1-100 mM |
| | Phosphate citrate buffer | *q.s. for 1-100 mM |
| | NaOH/Trolamine | *q.s. for 1-100 mM |
| | Lactate buffer | *q.s. for 1-100 mM |
| | Borate buffer | *q.s. for 1-100 mM |
| | Borate citrate | *q.s. for 1-100 mM |
| Preservatives | None - Non preserved | NA |
| | BAK | 10-200 ppm |
| | Purite | 10-300 ppm |
| Diluent/bulking agent/cake formers | Mannitol | q.s. to 100% |
| | Lactose | q.s. to 100% |
| | Trehalose | q.s. to 100% |

TABLE 4

Examples of Part 2 liquids for a two-part formulation system

| Ingredient type | Ingredient | Examples of typical conc. range % (w/w) |
|---|---|---|
| Following ingredients may or may not be included in the formulation Part 2 | | |
| Suspending agents/viscosity enhancer (may or may not be required) | Hydroxypropyl Methyl Cellulose | 0-7% |
| | Sodium Hyaluronate | 0-5% |
| | Carboxymethyl Cellulose | 0-8% |
| | Hydroxyethyl Cellulose | 0-6% |
| | Polyvinylpyrrolidone K90 | 0-25% |
| | Pluronic F127 | 0-15% |
| | Carbomer | 0-4% |
| Solubilizer/surfactant/dispersing agents (may or may not be required) | Polysorbate 80 | 0-4% |
| | Solutol HS 15 | 0-5% |
| | Pluronic F68 | 0-5% |
| | Cremophor RH40 | 0-5% |
| | Cremophor EL | 0-5% |
| | Pluronic F127 | 0-2% |
| | Sodium glycocholate | 0-2% |
| Osmolality agents (any one or two or more in combinations) | Potassium chloride | 0-2% |
| | Mannitol | 0-5% |
| | Sodium chloride | 0-1% |
| Buffers (Any one or more of the buffers listed) | Phosphate buffer | *q.s. for 1-100 mM |
| | Phosphate citrate buffer | *q.s. for 1-100 mM |
| | NaOH/Trolamine | *q.s. for 1-100 mM |
| | Lactate buffer | *q.s. for 1-100 mM |
| | Borate buffer | *q.s. for 1-100 mM |
| | Borate citrate | *q.s. for 1-100 mM |
| Preservatives | None - Non preserved | NA |
| | BAK | 10-200 ppm |
| | Purite | 10-300 ppm |
| Vehicle | Water | QS |
| pH range | n/a | pH 5 to 8 |

For example, according to an embodiment, a suspension formulation can include Form 1 cyclosporin A, a suspending agent, a surfactant, an osmolality agent, one or more buffers, one or a bulking agent, and a vehicle. According to an embodiment, a suspension formulation can include Form 2 cyclosporin A, a suspending agent, one or more surfactants, a osmolality agent, one or more buffers, one or more bulking agents, and a vehicle. In an embodiment, the suspension formulation comprises, consists of, or consists essentially of cyclosporin A, sodium hyaluronate, poloxamer 407, sodium phosphate dibasic heptahydrate, sodium phosphate monobasic monohydrate, sodium chloride, sodium hydroxide or hydrochloric acid, and water. In another embodiment, the suspension formulation comprises, consists of, or consists essentially of cyclosporin A, sodium hyaluronate, polysorbate 80, sodium phosphate dibasic heptahydrate, sodium phosphate monobasic monohydrate, sodium chloride, sodium hydroxide or hydrochloric acid, and water. In an embodiment, the suspension formulation comprises, consists of, or consists essentially of cyclosporin A, sodium hyaluronate, poloxamer 407, mannitol, sodium phosphate dibasic heptahydrate, sodium phosphate monobasic monohydrate, and water.

Methods for Treatment

According to an embodiment, a method for treating an ocular condition includes administering a suspension formulation, such as the formulations disclosed herein, to a periocular area of an eye of a human or animal patient, and preferably a living human or animal. In some embodiments, a method of treating a patient may include injecting the suspension into the sub-conjunctival space or the sub-tenon space. In some embodiments, a method of treating a patient may comprise administering an implant to the patient by at least one of intravitreal injection, subconjunctival injection, subtenon injections, retrobulbar injection, and suprachoroidal injection.

In at least one embodiment, a method of treating an ocular surface disease, such as dry eye/keratoconjunctivitis sicca, meibornian gland disease, atopic keratitis, blepharitis, and the like in a patient comprises administering one or more suspensions, as disclosed herein, to a patient by at least one of subconjunctival injection, sub-tenon injection, intracameral injection, retrobuibar injection, and suprachoroidal injection.

A syringe apparatus including an appropriately sized needle, for example, a 22 gauge needle, a 23 gauge needle, a 25 gauge needle, a 27 gauge needle, a 29 gauge needle, or a 30 gauge needle, can be effectively used to inject the composition into the subconjunctival space of an eye of a human or animal. According to some embodiments, no more than one injection is administered to the patient to treat the condition. According to other embodiments, more than one injection is administered to the patient to treat the condition.

EXAMPLES

Without intending to limit the scope of the disclosure, example embodiments are set forth by the following Examples.

Example 1

In a single dose CsA subconjunctival injection tolerability study in rabbits, New Zealand White rabbits (5 males/group) were given a single subconjunctival injection into each eye of 1 of 10 example formulations followed by a 29-day observation period. Ten different treatments of CsA (designated as Treatments A-J) were made with variations in the CsA lot, crystalline form, Sodium Hyaluronate manufacturer, CsA particle size, and residual PEG content/degradants, and injection location. Compositions of test formulations are listed in Table 5.

TABLE 5

Compositions of Test Formulations according to Example 1

| | % (w/w) | |
|---|---|---|
| Ingredient | Treatment H | Treatments A-G, I and J |
| CsA Form 1 | 20 | NA |
| CsA Form 2 | NA | 20 |
| Sodium Hyaluronate (HA) | 2 | 2 |
| Sodium Chloride | 0.85 | 0.85 |
| Sodium Phosphate Dibasic Heptahydrate | 0.27 | 0.27 |
| Sodium Phosphate Monobasic Monohydrate | 0.03 | 0.03 |
| Water for Injection | q.s. | q.s. |
| Total | 100 | 100 |

The slit lamp results plotted in FIG. 1 showed that at 7 days post injection, hyperemia scores were comparable (mild to moderate) in all treatment groups. By Day 29, Treatment H (CsA Crystal Form 1) showed faster hyperemia resolution.

Histopathology evaluation identified Treatment H formulation (containing cyclosporin A Form 1) as the best tolerated formulation based on the minimal tissue reaction and absence of granulomas. Treatment H was associated with tissue impression casts of the drug depot at the injection site, with a minimal granulomatous infiltrate. The injection sites of eyes from all of the other formulations (various treatments of CsA Crystal Form 2; Treatments A-G, I and J) were associated with granulomas that varied from minimal to moderate. Results by severity are summarized in Table 6.

TABLE 6

Summary of Cyclosporin Injection Site Granulomas by Severity

| | Cyclosporin Crystal | | | | | | | | | |
|---|---|---|---|---|---|---|---|---|---|---|
| | Form 1 | Form 2 | | | | | | | | |
| | Treatment | | | | | | | | | |
| Score, N | H 5 | A 5 | B 5 | C 5 | D 5 | E 5 | F 5 | G 5 | I 5 | J 5 |
| Minimal | 0 | 1 | 3 | 0 | 0 | 2 | 1 | 0 | 0 | 0 |
| Mild | 0 | 4 | 2 | 3 | 4 | 3 | 2 | 2 | 1 | 1 |
| Moderate | 0 | 0 | 0 | 2 | 1 | 0 | 2 | 3 | 4 | 4 |

Example 2

In another study, CsA in different solid forms (Form 1, Form 2 and Amorphous form) formulated in the same vehicle were administered as a single 50 μL subconjunctival injection to Beagle dogs, followed by a 29-day observation period. Compositions of test formulations are listed in Table 7. Each test formulation contained 5% CsA suspended in a vehicle containing 0.25% hyaluronic acid (HA) and 0.1% Polysorbate 80 (PS80) in phosphate buffered saline. The solid forms of cyclosporin A in the test formulations were Crystal Form 1 (F1), Crystal Form 2 (F2), and Amorphous Form (Am), respectively.

TABLE 7

Compositions of Test Formulations in the Example 2 Study

| | 5% CsA F1/ 0.25% HA/ 0.1% PS80 | 5% CsA F2/ 0.25% HA/ 0.1% PS80 | 5% CsA Am/ 0.25% HA/ 0.1% PS80 | Vehicle |
|---|---|---|---|---|
| CsA Solid Form Delivery Format | Crystal Form 1 Reconstituted suspension | Crystal Form 2 Pre-made suspension | Amorphous Form Reconstituted suspension | NA Solution |
| Ingredient | % w/w | | | |
| CsA | 5 | 5 | 5 | 0 |
| Sodium Hyaluronate (HA) | 0.25 | 0.25 | 0.25 | 0.26 |
| Polysorbate 80 | 0.1 | 0.1 | 0.1 | 0.11 |
| Sodium Chloride | 0.82 | 0.82 | 0.82 | 0.86 |
| Sodium Phosphate Dibasic Heptahydrate | 0.26 | 0.26 | 0.26 | 0.27 |
| Sodium Phosphate Monobasic Monohydrate | 0.03 | 0.03 | 0.03 | 0.03 |
| Water for Injection | Fill to 100% | Fill to 100% | Fill to 100% | Fill to 100% |

Figure 2A:
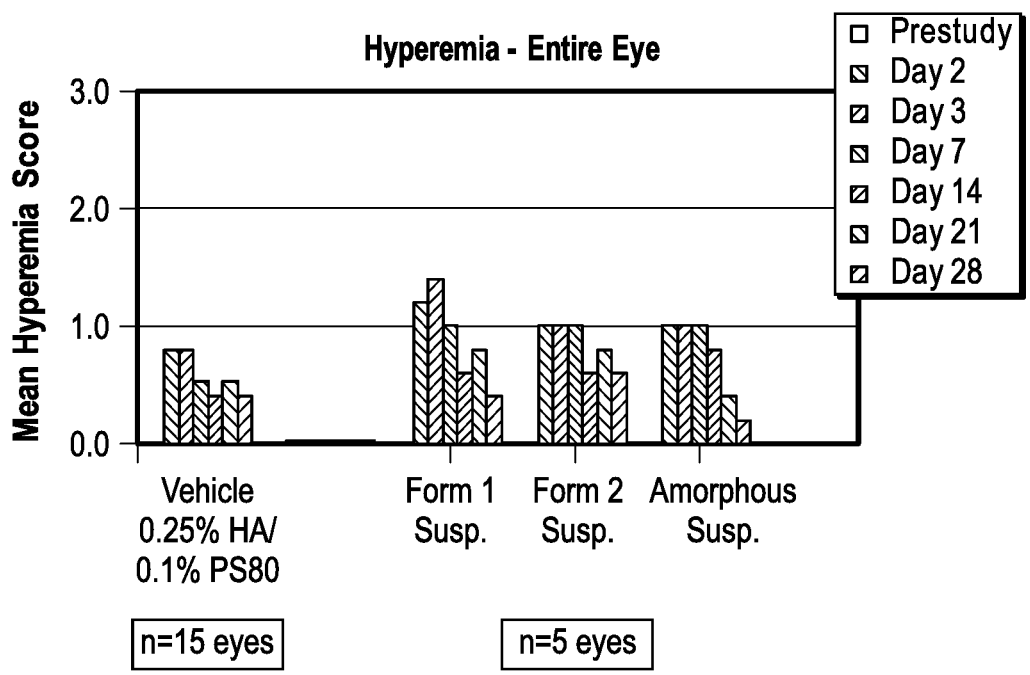
FIGS. 2A and 2B each show a comparison of conjunctival hyperemia scores of various embodiment suspension formulations used in the Example 2 study.
Figure 2B:
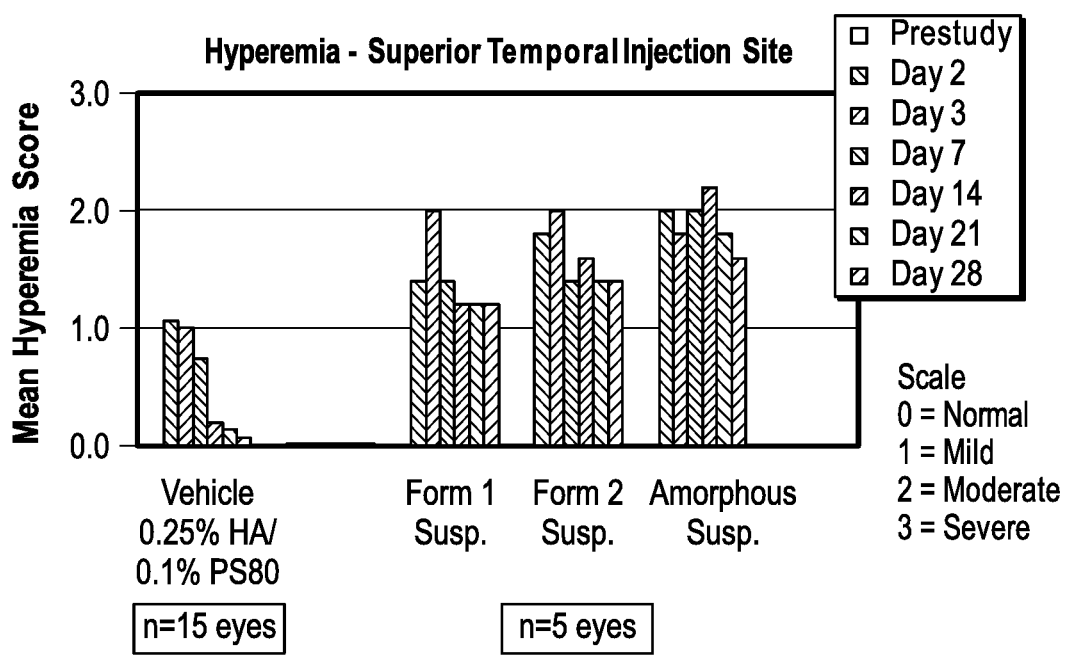

In the study, gross ocular observations were made on each eye once predose, and on Days 2, 3, 7, 14, 21, and 28. Gross ocular observations included, but was not limited to, hyperemia, swelling, and discharge. Hyperemia and swelling were scored and plotted for the entire eye and at each of the injection sites. FIG. 2 showed that the CsA Form 1 suspension resulted in the least severity of hyperemia, and then followed by CsA Form 2 suspension, and CsA amorphous form suspension caused the most severity of hyperemia and had increase in severity to +3 (severe) on Day 14. For the vehicle of 0.25% HA/0.1% PS80 in phosphate buffered saline, conjunctival hyperemia resolved mostly by Day 14. Conjunctival swelling was only notable in three dogs for the amorphous formulation (FIG. 3). In addition, it was observed that CsA Form 1 suspension formed a deposit without extensive spreading at the injection site.

Example 3

In a study, CsA formulations were given as a single 50 μL, bulbar subconjunctival injection to New Zealand White (NZW) rabbits followed by a 29-day observation period. One of the objectives of the study is to evaluate the tolerability and histopathology of CsA Form 1 formulations with different particle size distribution. Compositions and particle size distribution data of test CsA Form 1 formulations are summarized in Table 8. Treatment R was made from a CsA Form 1 lot which was jet milled with a $D_{90}$ particle size of 18.2 μm, and Treatments Q, S and T were made from the same lot of CsA but sieved through a screen with hole size of 106 μm (such that the $D_{90}$ particle size was in the range of 70 μm to 100 μm).

TABLE 8

Compositions and Particle Size Distribution Data of CsA Form 1 Test Formulations in the Example 3 Study

| Ingredient | | % (w/w) | | | |
|---|---|---|---|---|---|
| | | Treatment Q | Treatment R | Treatment S | Treatment T |
| CsA Form 1 | | 20 | 20 | 10 | 20 |
| Hydroxyethyl Cellulose (HEC) | | 0.1 | NA | NA | NA |
| Sodium Hyaluronate (HA) | | NA | 0.5 | 0.5 | 0.5 |
| Sodium Chloride | | 0.52 | 0.65 | 0.66 | 0.52 |
| Sodium Phosphate Dibasic Heptahydrate | | 0.16 | 0.21 | 0.21 | 0.16 |
| Sodium Phosphate Monobasic Monohydrate | | 0.02 | 0.02 | 0.02 | 0.02 |
| Water for Injection | | q.s. | q.s. | q.s. | q.s. |
| Total | | 100 | 100 | 100 | 100 |
| Particle Size Distribution (μm) | $d_{90}$ | 70.16 | 18.23 | 100.67 | 77.36 |
| | $d_{50}$ | 25.44 | 12.04 | 36.6 | 27.73 |
| | $d_{10}$ | 10.32 | 7.67 | 12.66 | 11.21 |

In the study, gross ocular observations were recorded for each eye on Days 3, 5, 7, 14, 21, and 29. Conjunctival hyperemia scores were recorded for the entire eye and at the injection (depot) site. As shown in FIG. 4, comparison of the four treatments based on conjunctival hyperemia scores for the entire eye showed better resolution for Treatments Q, S and T (CsA Form 1 sieved large). The hyperemia at the depot site was relatively the same for all four treatments.

Example 4

In a study, CsA formulations were dosed as a single 50 μL bulbar subconjunctival injection to New Zealand White (NZW) rabbits followed by a 7-day observation period.

Ocular tolerability of three CsA prototype formulations, including prefilled-syringe gel of CsA Form 2 in HA, reconstituted suspensions of CsA Form 1 in HA and hydroxymethylcellulose (HPMC), was evaluated in rabbits. Formulation compositions are listed in Table 9.

TABLE 9

Compositions of Test CsA Formulations in the Example 4 Study

| | Reference Formulation 1 (F2/2% HA) | Prototype Formulation 1 (F2/2% HA) | | Prototype Formulation 2 (F1/0.15% HA) | | | Prototype Formulation 3 (F1/0.5% HPMC) | | |
|---|---|---|---|---|---|---|---|---|---|
| CsA Solid Form | Form 2 | Form 2 | | Form 1 | | | Form 1 | | |
| Delivery Format | Prefilled syringe | Prefilled syringe | | Reconstituted suspension | | | Reconstituted suspension | | |
| Ingredient | | | | % w/w | | | | | |
| Treatment | U | Y | Z | W | AA | AB | X | AC | AD |
| CsA | 20 | 2 | 10 | 0 | 2 | 10 | 0 | 2 | 10 |
| Sodium hyaluronate (HA) | 2.0 | 2.0 | | | 0.15 | | | NA | |
| Hydroxymethyl-Cellulose (HPMC) | NA | NA | | | NA | | | 0.5 | |
| Polysorbate 80 | NA | NA | | | 2.0 | | | 2.0 | |
| Sodium Chloride | 0.87 | 0.82 | | | 0.82 | | | 0.82 | |

TABLE 9-continued

Compositions of Test CsA Formulations in the Example 4 Study

| | Reference Formulation 1 (F2/2% HA) | Prototype Formulation 1 (F2/2% HA) | Prototype Formulation 2 (F1/0.15% HA) | Prototype Formulation 3 (F1/0.5% HPMC) |
|---|---|---|---|---|
| Sodium Phosphate Dibasic Heptahydrate | 0.28 | 0.26 | 0.26 | 0.26 |
| Sodium Phosphate Monobasic Monohydrate | 0.03 | 0.03 | 0.03 | 0.03 |
| Water for Injection | Fill to 100% | Fill to 100% | Fill to 100% | Fill to 100% |

Figure 5A:
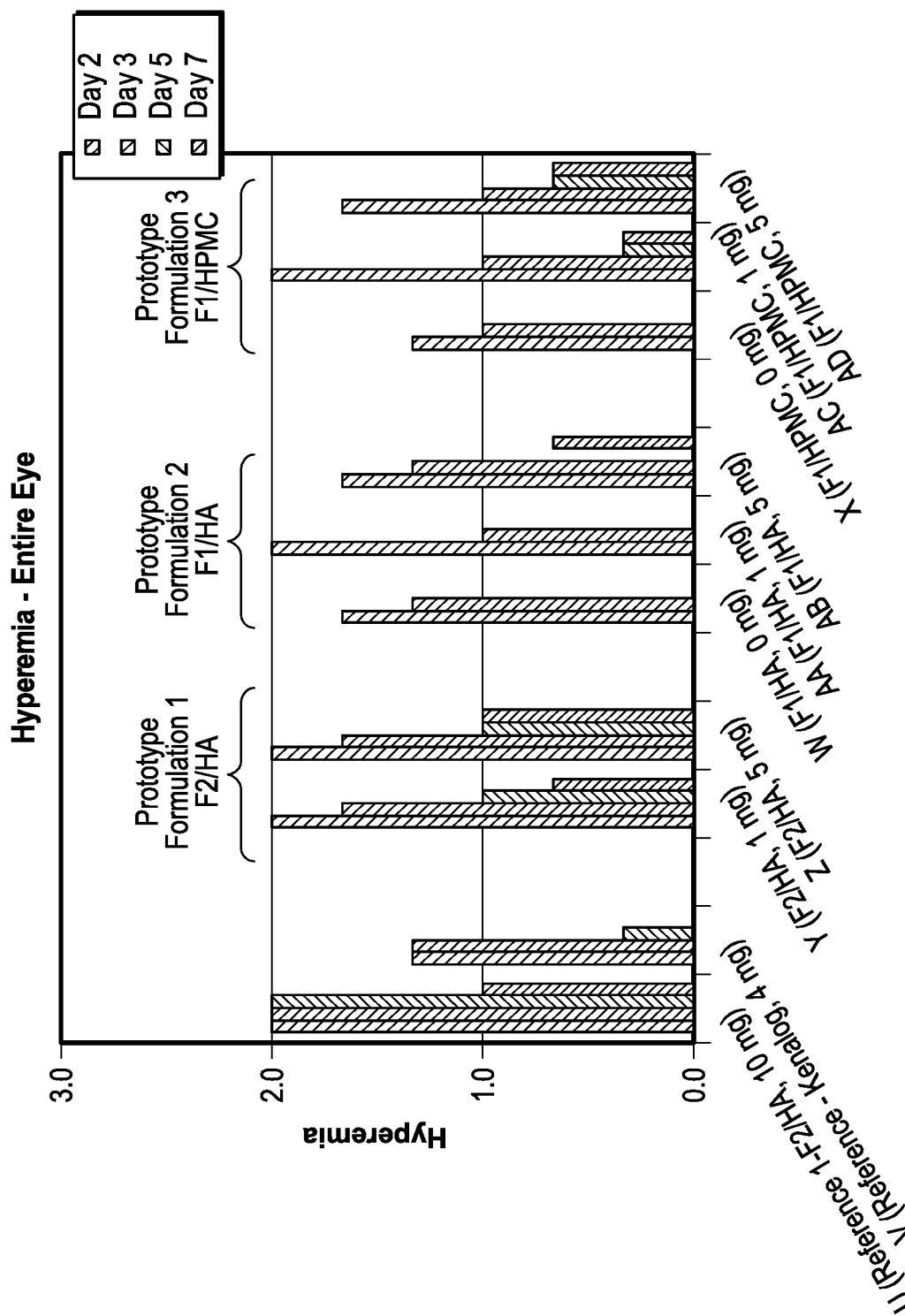
FIGS. 5A and 5B each show a comparison of conjunctival hyperemia scores in the entire eye and at the injection site, respectively, of various embodiment suspension formulations used in the Example 4 study.
Figure 5B:
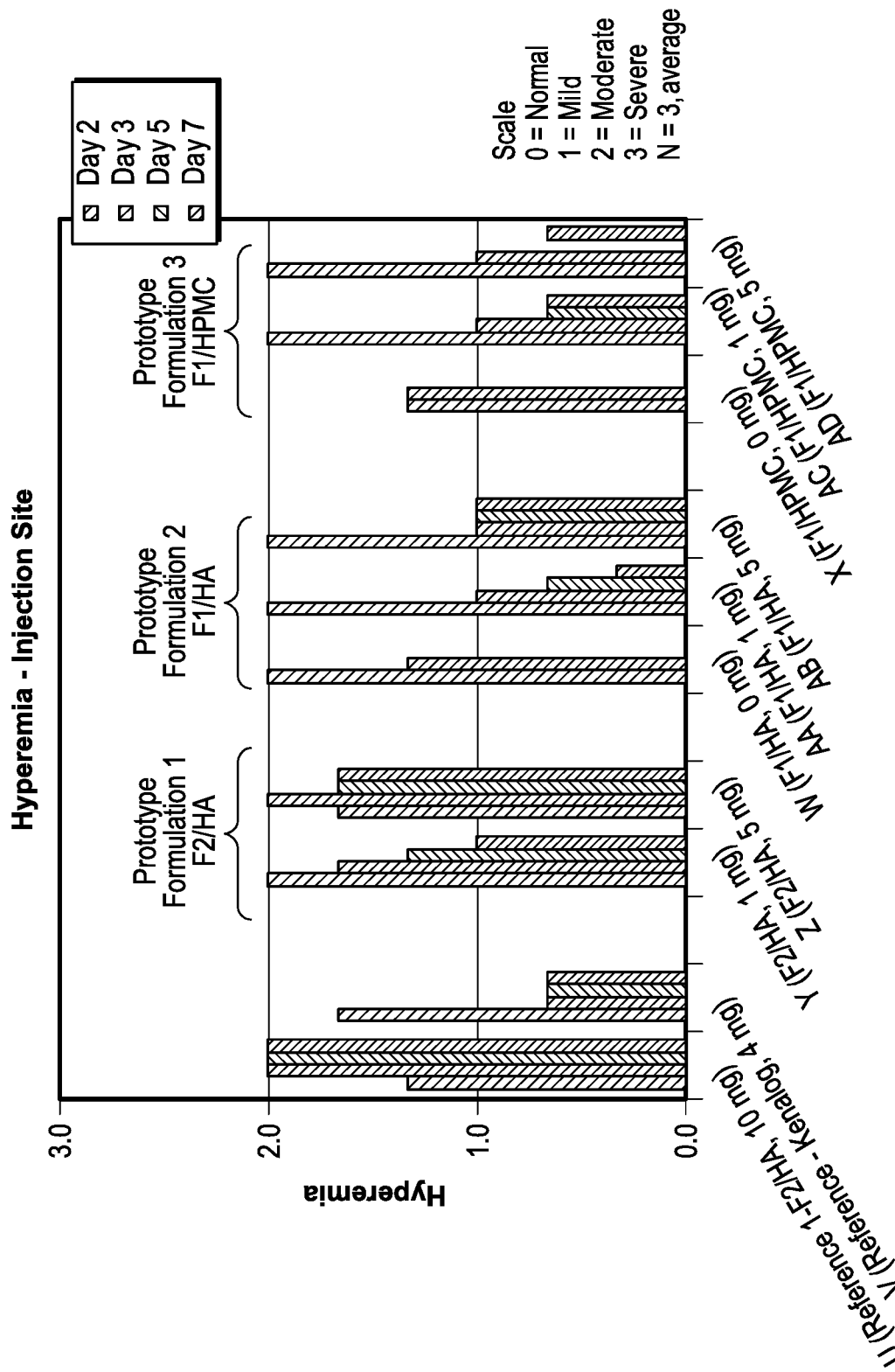

In this study, gross ocular observations were made on each eye once predose on Day 1, and on Days 2, 3, 5, and 7. Conjunctival hyperemia scores for the entire eye and at the injection site are plotted in FIG. 5. Eyes treated with formulations containing CsA Form 1 in HA (Prototype Formulation 2) showed less hyperemia than those treated with formulations containing CsA Form 2 in HA (Prototype Formulation 1) or CsA Form 1 in HPMC (Prototype Formulation 2).

Example 5

Suspensions of CsA Form 1 may be provided as a 1-part system which is stored at frozen (below −2° C.), with the temperature range being −70° C. to −2° C., to ensure physical stability of CsA Form 1. When these formulations are dispensed to the patient, they would be kept at room temperature or at ambient conditions to thaw the product and bring it back to its liquid state. This concept would be advantageous for formulations with chemically or physically labile compounds. The physical stability data of CsA Form 1 suspensions stored at frozen are included in Example 8.

Example 6

Suspensions of CsA Form 1 may be provided as a pre-filled syringe which is stored at frozen (below −2° C.) or refrigerated (2-8° C.) conditions to ensure physical stability of CsA Form 1. The formulations are allowed to equilibrate to ambient conditions prior to dosing. Test formulations of CsA Form 1 listed in the Examples 1 and 3 were provided as pre-filled syringe.

Example 7

Suspension formulation can be provided by a 2-part system and prepared by reconstitution prior to dosing. In this system, the first part of the formulation may be a solid, containing either the drug substance either alone, or in a formulation matrix that maximizes its stability and shelf-life. The solid may be manufactured by lyophilization, spray-drying, blending, milling, granulation or other pharmaceutical processing. The second part would be a formulation vehicle suitable for sub-conjunctival injection. When the two parts are mixed, the final product would be acceptable for sub-conjunctival injection with a shelf-life sufficient for the duration of the use of the product. Test formulations of CsA Form 1 listed in the Examples 2 and 4 were provided by reconstituting drug powder with a vehicle prior to dose administration.

Example 8

Figure 6:
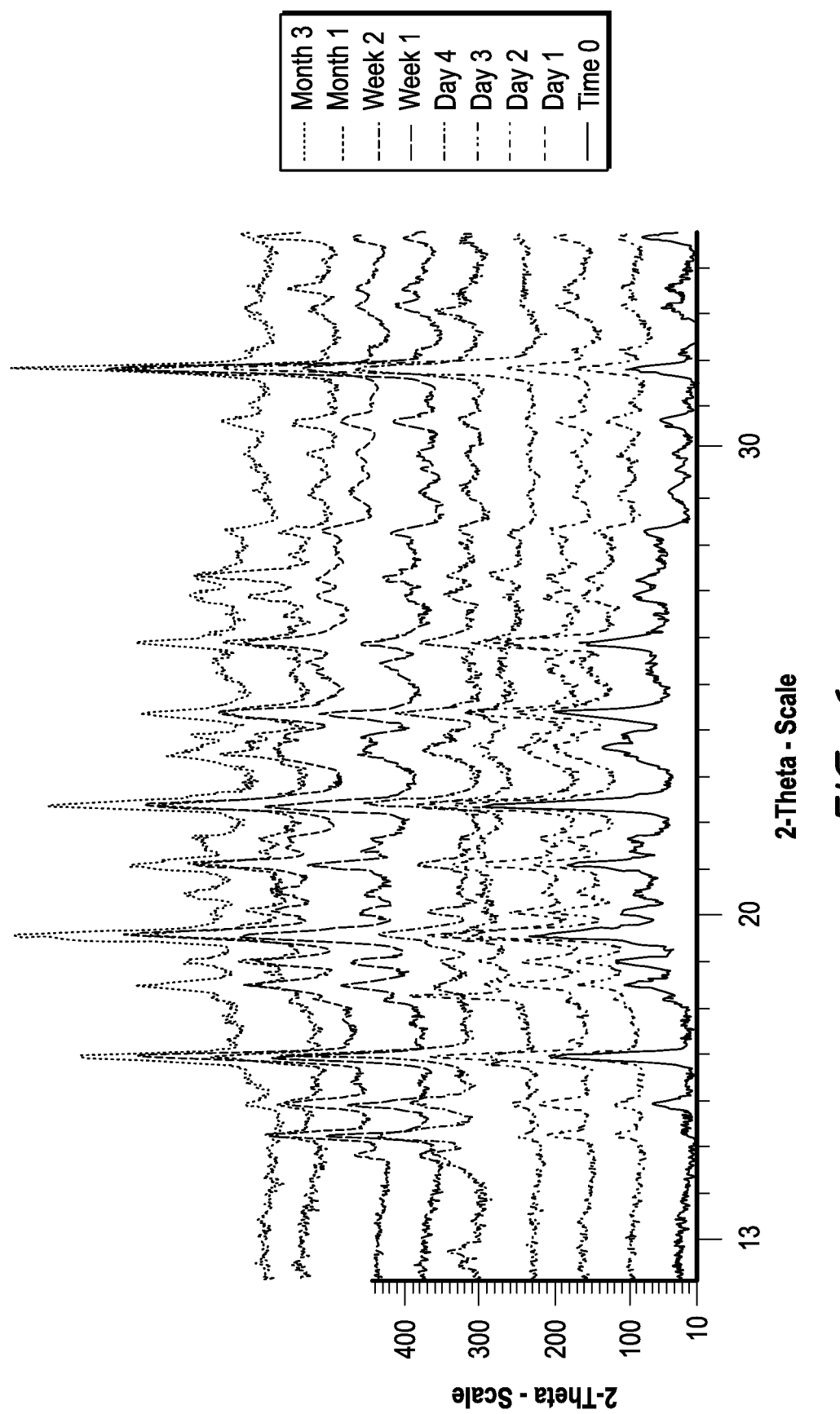
FIG. 6 illustrates the XRPD patterns of 5% CsA F1/1% HPMC/2% Polysorbate 80 suspension stored at −20° C.
Figure 7:
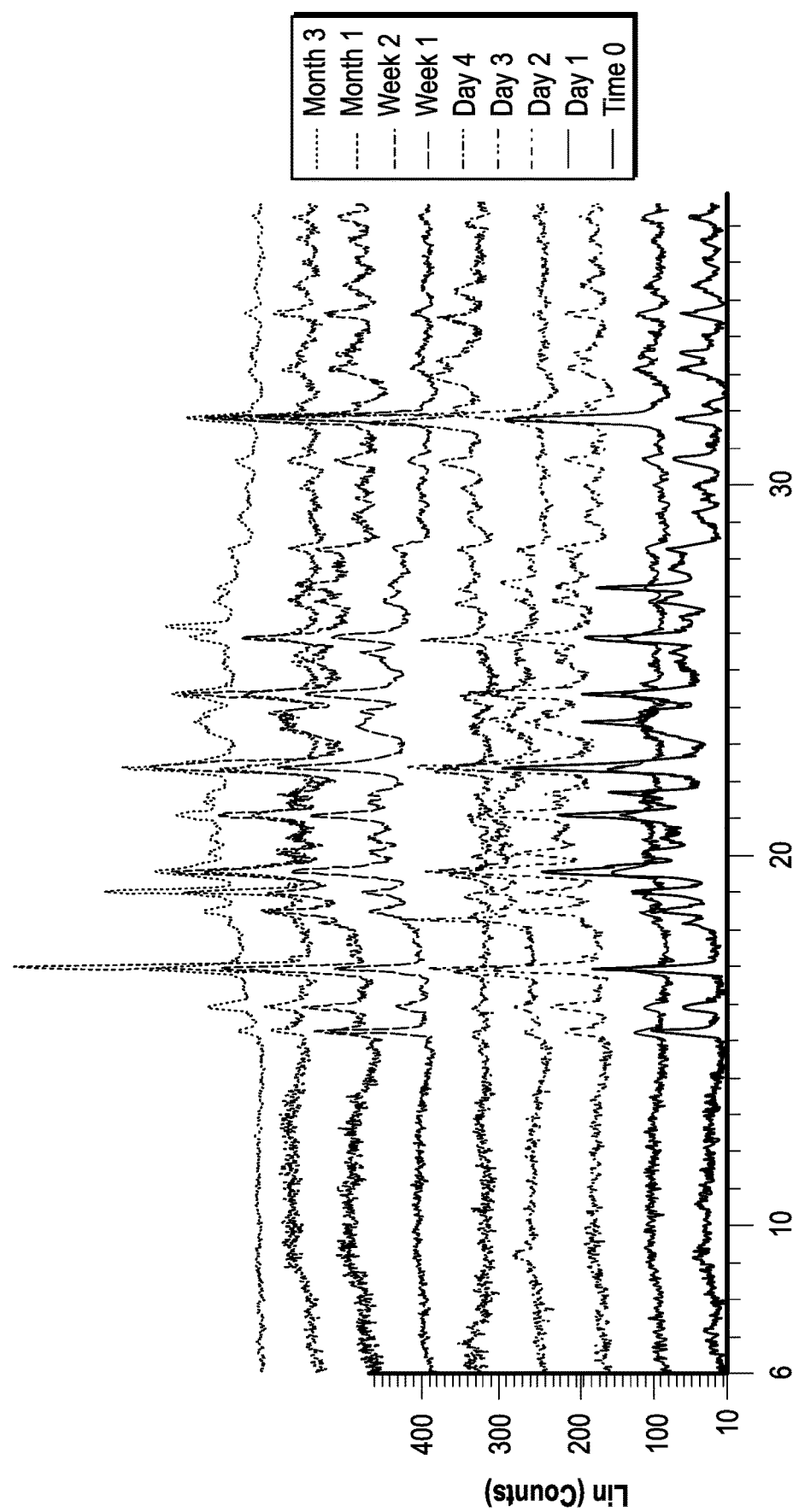
FIG. 7 illustrates the XRPD patterns of 10% CsA F1/1% HPMC/2% Polysorbate 80 suspension stored at −20° C.
Figure 8:
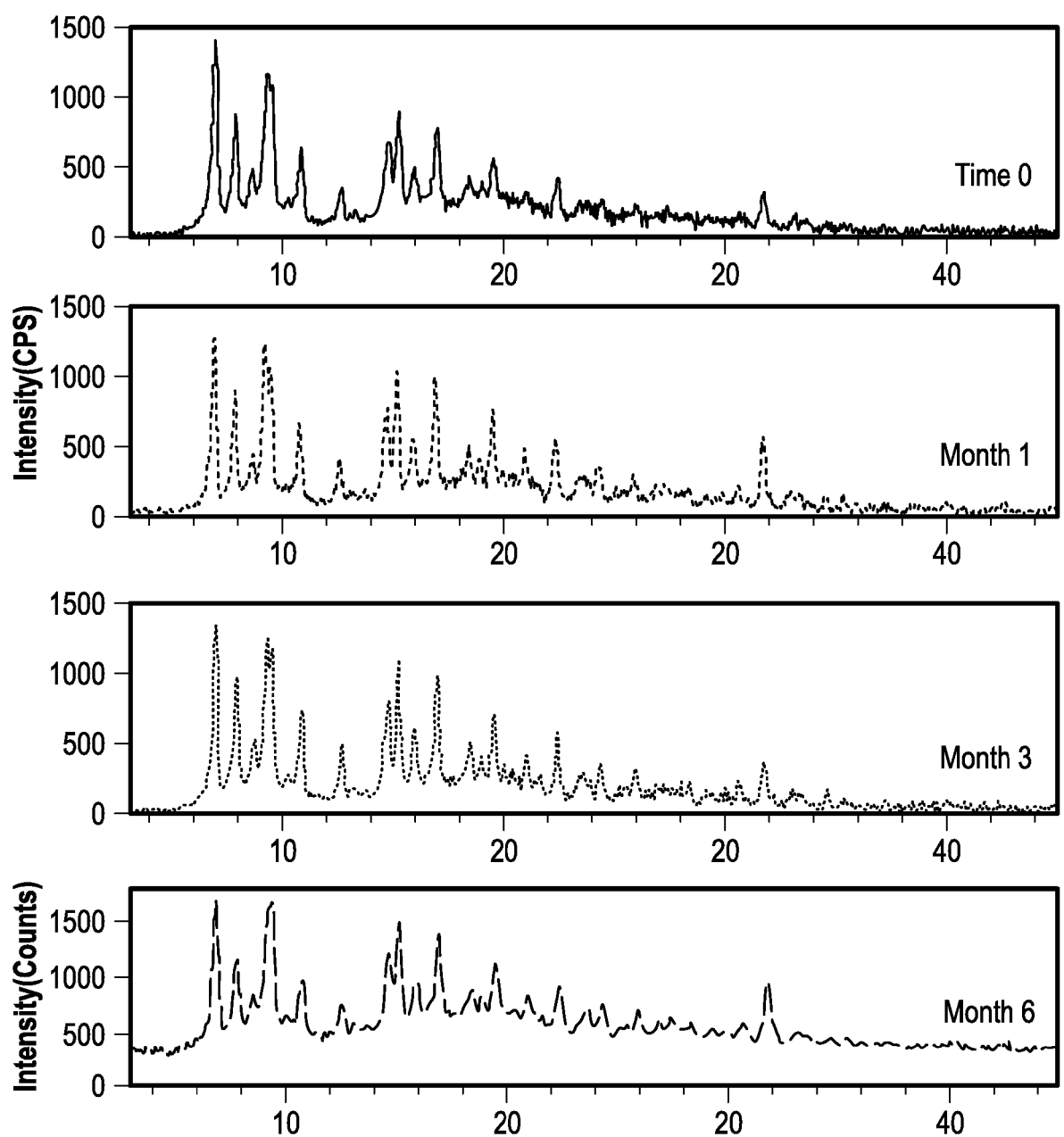
FIG. 8 illustrates the XRPD patterns of 5% CsA F1/0.25% HA/0.1% Polysorbate 80 suspension stored at −20° C.

In a study of assessing the physical stability of CsA Form 1 in suspension formulations, CsA solids prepared from samples stored at frozen were examined for physical form identification using X-ray powder diffraction (XRPD) at predetermined time points. The compositions of formulations in the study are summarized in Table 10, FIG. 6 display the XRPD patterns of these formulations upon storage at −20C. for up to 3 months, respectively,

TABLE 10

Compositions of CsA Form 1 Formulations in the physical stability study

| | % (w/w) | | |
|---|---|---|---|
| Ingredient | 5% CsA F1/ 1% HPMC/ 2% PS80 | 10% CsA F1/ 1% HPMC/ 2% PS80 | 5% CsA F1/ 0.25% HA/ 0.1% PS80 |
| CsA Form 1 | 5 | 10 | 5 |
| Sodium Hyaluronate (HA) | — | — | 0.25 |
| Hydroxymethyl-Cellulose (HPMC) | 1 | 1 | — |
| Polysorbate 80 | 2 | 2 | 0.1 |
| Sodium Chloride | 0.82 | 0.82 | 0.82 |
| Sodium Phosphate Dibasic Heptahydrate | 0.26 | 0.26 | 0.26 |
| Sodium Phosphate Monobasic Monohydrate | 0.03 | 0.03 | 0.03 |
| Water for Injection | Fill to 100% | Fill to 100% | Fill to 100% |

It is clear that there was no observable evolution in the XRPD patterns, which suggests that CsA Form 1 appeared to be physically stable for at least 6 months in these formulations stored at frozen.

Example 9

The following other example cyclosporin A suspension formulations were created and tested in a rabbit tolerability and pharmacokinetics study. The example formulations are described in Tables 11-12. The formulations in Table 11 were prepared as two-part systems, then reconstituted prior to dosing.

TABLE 11

Compositions of CsA Form 1 Formulations tested in rabbit tolerability & pharmacokinetics study.

| Ingredient | Concentration (% w/w) | | |
|---|---|---|---|
| | F1 lyophilized | F1 Drug in Vial | F1 Drug in Vial |
| Cyclosporine (CsA) | 5 or 10 (F1 lyophilized) | 5 or 10 or 20 | 5 or 10 or 20 |
| Sodium Hyaluronate (HA) | 0.25 | 0.4 | 0.25 |
| Polysorbate 80 | — | 0.5 | 0.10 |
| Poloxamer 407 | 0.10 | — | — |
| Mannitol | 4.00 | 4.00 | 4.00 |
| Sodium Phosphate Dibasic Heptahydrate | 0.26 | 0.26 | 0.26 |
| Sodium Phosphate Monobasic Monohydrate | 0.03 | 0.03 | 0.03 |
| Sodium Chloride | — | 0.82 | 0.82 |
| Water for Injection | Fill to 100% | Fill to 100% | Fill to 100% |

Formulations were well tolerated over 28 days in rabbits after a single subconjuctival injection. At the end of 28 days, the levels of CsA in ocular tissues were found to be similar for all three formulations across the same concentration.

TABLE 12

Compositions of CsA Form 2 Formulations tested in rabbit tolerability study.

| Ingredient | Concentration (% w/w) | |
|---|---|---|
| | F2 DIV or F2 pre-made | F2 DIV suspension |
| Cyclosporine (CsA) | 5 or 10 or 20 | 5 or 10 or 20 |
| Sodium Hyaluronate (HA) | 0.40 | 0.26 |
| Polysorbate 80 | — | 0.11 |
| Poloxamer 407 | 0.50 | — |
| Sodium Phosphate Dibasic Heptahydrate | 0.26 | 0.27 |
| Sodium Phosphate Monobasic Monohydrate | 0.03 | 0.03 |
| Sodium Chloride | 0.82 | 0.86 |
| Sodium hydroxide or Hydrochloric acid | pH adjust to 7.0 | pH adjust to 7.0 |
| Water for Injection | Fill to 100% | Fill to 100% |

The above-listed formulations were well tolerated over 28 days in rabbits after a single subconjunctival injection.

Formulations were prepared either as two-part system and reconstituted prior to dosing or made as suspensions and filled in glass vials.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition while the number of variations of the invention have been shown and described in detail, other modifications, which are within the scope of this invention, will be readily apparent to those of skill in the art based on this disclosure. It is also contemplated that various combinations or subcombinations of the specific features and aspects of the embodiments can be made and still fall within the scope of the invention. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A liquid suspension formulation for subconjunctival injection into the eye of a human, the suspension formulation comprising:
   cyclosporin A Form 1 in an amount of between 5% by weight to about 20% by weight;
   a viscosity enhancer selected from the group consisting of hyaluronic acid and hydroxyethyl cellulose;
   sodium chloride;
   a phosphate buffer; and
   a vehicle;
   wherein the cyclosporin A has a $D_{50}$ particle size in the range of about 10 μm to about 50 μm and a $D_{90}$ particle size in the range of about 70 μm to about 100 μm.

2. The suspension formulation of claim 1, wherein the cyclosporin A is present in the suspension formulation in an amount of about 20% w/w.

3. The suspension formulation of claim 1, wherein the cyclosporin A is present in the suspension formulation in an amount of about 10% w/w.

4. The suspension formulation of claim 1, further comprising a pre-filled syringe, wherein the suspension formulation is contained inside the pre-filled syringe.

5. The suspension formulation of claim 4, wherein the suspension formulation is frozen at a temperature in the range of about −70° C. to about −2° C.

* * * * *